US00PP23690P3

(12) United States Plant Patent
Zwetzig

(10) Patent No.: US PP23,690 P3
(45) Date of Patent: Jun. 25, 2013

(54) ***HIBISCUS* PLANT NAMED 'KUI NUKU'**

(50) Latin Name: *Hibiscus moscheutos×H. coccineus*
Varietal Denomination: Kui Nuku

(75) Inventor: Gretchen Zwetzig, Lindsay, CA (US)

(73) Assignee: Gretchen Zwetzig, Luidsay, CA (US)

( * ) Notice: Subject to any disclaimer, the term of this patent is extended or adjusted under 35 U.S.C. 154(b) by 118 days.

(21) Appl. No.: 12/932,359

(22) Filed: Feb. 24, 2011

(65) Prior Publication Data

US 2012/0222178 P1 Aug. 30, 2012

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — June Hwu

(57) ABSTRACT

A new and distinct cultivar of winter hardy *Hibiscus* plant named 'Kui Nuku' is the result of a unique hybridization. This new and distinct cultivar is characterized primarily as to its novelty by its extreme cold hardiness to Zone 4, large thick-textured, magenta-pink flowers and its "Maple-shaped" leaves with a purple coloration, compactness of about 3 feet, its vigorous and uniform growth habit and its floriferous nature from midsummer until frost.

1 Drawing Sheet

Latin name: *Hibiscus moscheutos×H. coccineus.*
Varietal denomination: 'Kui Nuku', hardy *Hibiscus.*

FIELD OF THE INVENTION

This plant, as a hybridized hardy *Hibiscus*, is valuable to the landscape market for its improvements in thicker textured and brightly colored flowers and buds, refined "maple-like" foliage with a purple color, its all-around vigor, compact breaking action, and adaptation to extreme environments, including the ability to consistently survive winter temperatures of at least −30 degrees Fahrenheit.

BACKGROUND OF THE NEW PLANT

The new plant of this invention is the result of a unique hybridization, with the breeding achievement being evidenced in the outstanding combination of characteristics exhibited by this new and distinct *Hibiscus* plant, which include:

(a) Refined, 3-5 lobed 'maple-shaped' leaves with a purple color and relatively smooth margins which combined compliments the landscape;
(b) Medium-sized flowers that are outstanding for their luminescent magenta-pink colored, very overlapping thick textured petals;
(c) The plant being very floriferous with flowers that stay open for at least one full day, sometimes up to 2 days;
(d) The plant being small to medium-sized but vigorous with compact and uniform breaking action which gives it unique landscape utility; and
(e) The plant being so hardy that it can consistently withstand winter temperatures of at least −30 degrees Fahrenheit.

SUMMARY OF THE INVENTION

'Kui Nuku' was the result of a 50-year breeding program. Its ancestry includes *Hibiscus moscheutos* and *Hibiscus coccineus*. More specifically, the plant resulted from multiple crossings with an unnamed, Fleming-bred *Hibiscus moscheutos* (non patented) and an unnamed Fleming-bred *Hibiscus coccineus* (non patented). The seedling which most nearly met all of the above standards was selected.

This new plant first bloomed in the summer of 2001 and was selected by Gretchen Zwetzig on her property located at 8101 S. 14th St. Lincoln, Nebr. 68516. Asexual propagation of the plant by cuttings and root division in Lincoln, Nebr. has shown that the unique and distinguishing features of the plant are faithfully transmitted from generation to generation and appear to be fixed.

Since its origin, the plant has bloomed from midsummer until frost, while exhibiting the aforementioned distinctive characteristics. This hardy *Hibiscus* plant greatly contributes to the market with its, sheer beauty and utter refinement, its compact growth habit, its enhanced resistance to disease and insects, its stability through extremes in rain and drought, and its extreme hardiness.

BRIEF DESCRIPTION OF THE DRAWINGS

The flower and foliage of the cultivar are shown at 2½ years in the attached photographs.

More specifically, FIG. 1 is a close-up of the flower and the leaf with separate green-leaved plant in background.

The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color descriptions are in accordance with The Royal Horticultural Society Color Chart (2001), while general color recitations are consistent with ordinary American terminology.

'Kui Nuku' has not been observed under all possible environmental conditions. It is to be understood that the phenotype may vary significantly with variations in the environment such as temperature, light intensity, humidity, and day length without, however any difference in genotype of the plant. The following botanical characteristics and observations are gathered from the plant when grown in Lincoln, Nebr. (USDA Zone 4) and Lindsay, Calif. (USDA Zone 9).

THE PLANT

Parentage:

*Seed parent.*—*Hibiscus moscheutos,* unnamed and unpatented Fleming-bred seedling.

*Pollen parent.*—*Hibiscus coccineus,* unnamed and unpatented Fleming seedling.

Comparison between observed plant and parents: Observed Plant is 1 foot shorter than parents and has a darker purple leaf.

Comparison between observed plant and other known cultivars: Observed Plant is unique, but most similar to other Fleming patented hardy *Hibiscus*: 'James Fleming' U.S. Plant Pat. No. 21,434, 'Royal Gems' U.S. Plant Pat. No. 11,011, and the other patented Flemings hardy *Hibiscus* in that: (a) They are all compact at approximately 3 feet on average. (b) They are hardy to −30 degrees Fahrenheit. (c) They all have refined new leaf shapes and colors. Though 'Kui Nuku' has 'Oak-shaped' leaf. (d) They all have thick, flowers with new colors and combinations that bloom from the top to the bottom of the plant. In contrast to comparisons, 'Kui Nuku' has newer flower color of mauve.

Origin: A selected seedling from stated cross.

Type of plant: Hardy, herbaceous perennial.

Classification: Variety of hardy *Hibiscus* plant.

Propagation: Relatively easy to propagate by cuttings in approximately 2 weeks; holds its distinguishing characteristics through successive cuttings and divisions.

Size: About 2½ to 3 feet tall and about 2 feet wide.

Form: Symmetrical annual growth from perennial roots.

Habit: Upright and uniformly branched.

Growth: Vigorous; but compact. Full grown (3 ft) in 2 years.

Hardiness: Hardy to at least −30 degrees Fahrenheit.

General health: Plant is very disease resistant against rot, aphids, spider mites, scale, white fly etc.; sturdy through excessive drought, rain or wind.

Foliage:

1. *Arrangement*.—Alternate.
2. *Shape*.—Juvenile: 3-5 lobed "maple-shaped" leaves. Rounded base shape. Mature: Refined, "maple-shaped", 3-5 lobed leaf with entire to mildly serrate margins and acute apices; rounded base.
3. *Size*.—Mature leaf (petiole base to apex): Length is about 7 inches or 17.78 cm, width is about 5½ inches or 13.97 cm.
4. *Color*.—Young leaves (upper side) 147 A: (purple color) 59 A. Mature leaves: (upper side): 147 A, (purple color) 59 A. Veins: 61-A. Venation pattern: Palmate. Upper side mature leaf. Coloration of mature lower leaf surface: Closest to 137 C.
5. *Surface texture*.—Low sheen. Upper: Smooth. Lower: Semi-smooth.
6. *Petiole length*.—About 2¾ inches or 6.985 cm. Petiole diameter: 2 cm.
7. *Petiole color*.—146 B. Surface Texture: Semi-smooth.

Stems: The stems are stout at the base, becoming more slender toward the apices; coloration is consistent with the petiole. Length: 2-3 inches on average. Diameter: 2 cm. Internode length: 2 inches on average. Stem texture: Semi-smooth. Stem color: 147 B.

Blooming period: Profuse from July until frost.

Flower diameter: Medium to large; about 9½ inches (24.13 cm).

Borne: Singly in the leaf axils, from midpoint of stems upward.

Bloom duration: Individual bloom lasts at least one full day; possibly up to 3 days.

Form: Campanulate; petals are also very overlapping.

Average number of flowers per season: 300.

Bud:

1. *Length*.—About 2½ inches or (6.35 cm) on day before opening. Diameter: 1-2 inches.
2. *Color*.—60 B.
3. *Surface texture*.—Semi-glabrous.
4. *Duration*.—One week.

Corolla: Having five petals.

1. *Petal character and dimensions*.—Campanulate and very overlapping. (a) Length: About 4½ inches or 11.43 cm. (b) Width: About 4¾ inches or 12 cm.
2. *Coloration*.—Mauve medium pink. (a) Medium pink petals: Between 64 C and 67 C. Coloration of lower petal surface: 77-B and 61-B. Margin: 67 C. (b) Venation in petals: N 66. (c) Eye zone color: Between 46-A and 53-B. Size: 2 inches or 5 cm.
3. *Texture*.—Smooth.
4. *Substance*.—Thick.
5. *Shape*.—Campanulate and very overlapping.

Reproductive organs:

1. *Staminal column*.—Stamen along basal two-thirds. Staminal column average length: About 1¾ inches or (4.44 cm). Filament column length: 1¼"; 3.175 cm. Average no.: 100. Stamen color designation: 54 A and 56 D. Pollen color: 12-B.
2. *Style*.—Terminates upper one-third of staminal column. Length: ½"; 1.27 cm. Color: 4 B. Stigmatic lobe color: 4 B. Stigma average size: 1 cm.

Calyx: Connate at the base; about 2 inches or (4½ cm) in length. Average per flower: 1. Color: Between 146-A and 146-B (Inside and Out). Shape: 5-lobed, cupped and connate at base. Surface texture: Semi-smooth.

Stipules: None.

Epicalyx: Whorl of bracts.

1. *Shape*.—10-12 slender, sword-shaped bractlets.
2. *Length*.—About 1¼ inches or (4.8 cm).
3. *Color*.—143-A (Upper and Lower Surface).

Peduncle:

1. *Length*.—About 1½ inches or (5 cm).
2. *Strength*.—Stiff and sturdy. Texture: Semi-smooth.
3. *Color*.—Light to medium green with slight reddish-purple cast. 146-A with 61-C.

Seeds (fruit): Average Size: Type: Round shape. 1 cm. Color: Grey-brown. Average number: Less than 100.

It is claimed:

1. A new and distinct cultivar of hardy *Hibiscus* plant, as herein shown and described, characterized by its compact nature, refined purplish "maple-like" foliage of a purple coloration, its large bold, magenta-pink flowers, its vigor and its hardiness.

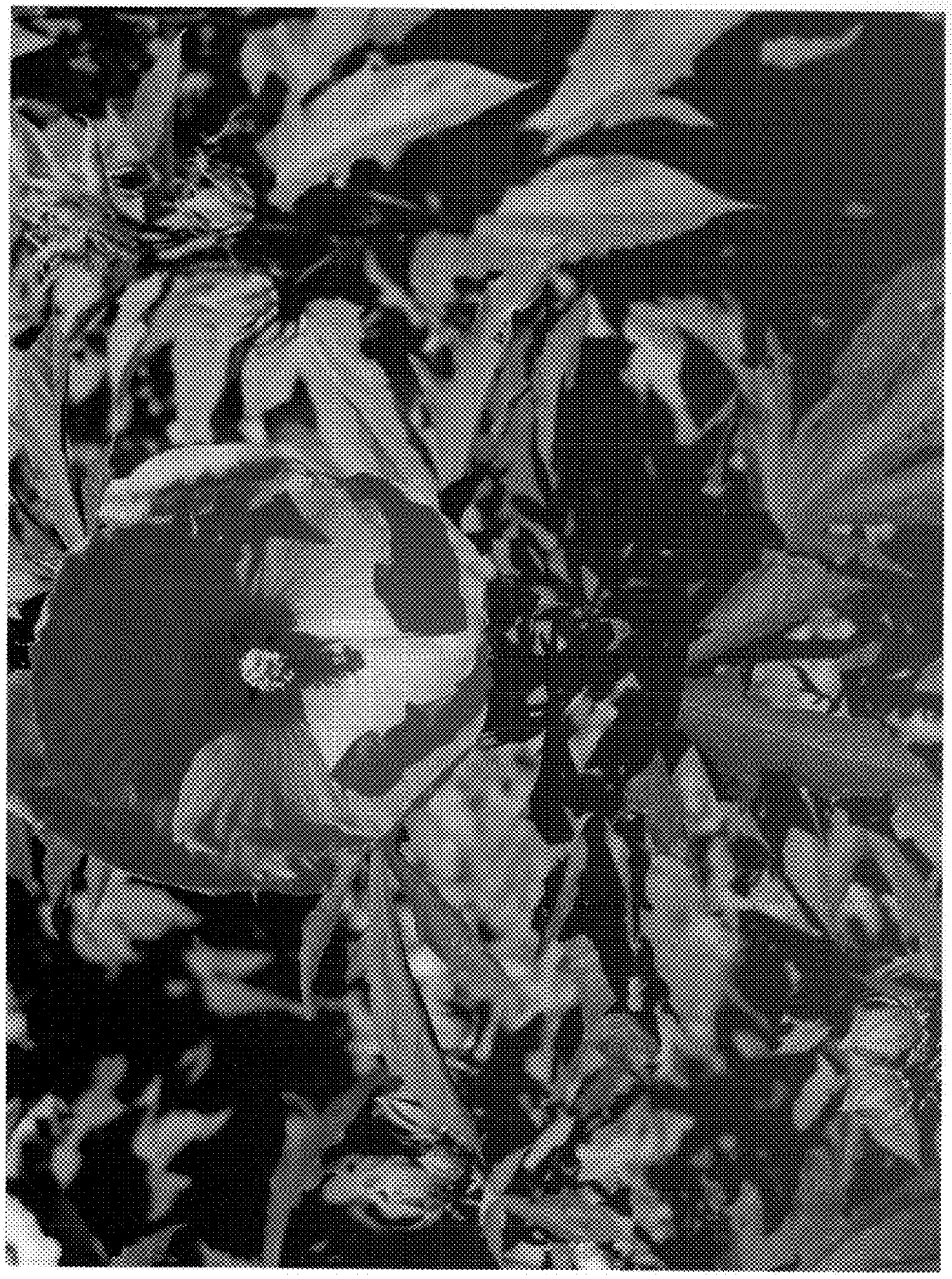

* * * * *